United States Patent [19]

Torri

[11] Patent Number: 4,552,141
[45] Date of Patent: Nov. 12, 1985

[54] ANESTHETIC RESPIRATORY SYSTEM

[75] Inventor: G. Torri, Milan, Italy

[73] Assignee: Drägerwerk Aktiengesellschaft, Fed. Rep. of Germany

[21] Appl. No.: 598,370

[22] Filed: Apr. 9, 1984

[30] Foreign Application Priority Data

Apr. 9, 1983 [EP] European Pat. Off. ........ 83103470.7

[51] Int. Cl.⁴ ............................................ A61M 16/00
[52] U.S. Cl. ............................ 128/205.12; 128/205.24; 128/203.28
[58] Field of Search ...................... 128/203.28, 203.29, 128/204.23, 205.12, 205.13, 205.14, 205.15, 205.16, 205.17, 205.24, 202.26

[56] References Cited

U.S. PATENT DOCUMENTS

| | | | |
|---|---|---|---|
| 2,099,841 | 11/1937 | Connell | 128/205.12 |
| 2,216,183 | 10/1940 | Connell | 128/205.24 |
| 2,403,991 | 7/1946 | Murphy et al. | 128/205.13 |
| 3,028,873 | 4/1962 | Kindred | 128/205.24 |
| 3,814,092 | 6/1974 | Simionescu et al. | 128/203.28 |

Primary Examiner—Henry J. Recla
Attorney, Agent, or Firm—McGlew and Tuttle

[57] ABSTRACT

An anesthetic respiratory system which is switchable between half-open and half-closed modes of operation improved with respect to the conspicuousness and operational safety. A $CO_2$ absorber is arranged in an expiration branch and is formed as a switching element detachable from connection points which are secured to a respirator housing. One point of connection of the absorber comprises a shut-off element positively actuated by the switching element, which upon removal of the absorber interrupts the ring line and establishes separate inspiration and expiration respiration branches. The second point of connection of the absorber is open upon removal and it lies behind the controllable outlet valve.

4 Claims, 2 Drawing Figures

ANESTHETIC RESPIRATORY SYSTEM

FIELD AND BACKGROUND OF THE INVENTION

This invention relates in general to anesthetic devices and in particular to a new and useful anesthetic respiratory system.

The invention relates to an anesthetic respiratory system for inhalation narcoses which is switchable from partial or total rebreathing to non-rebreathing modes of operation, with a ring line containing a $CO_2$ absorber and forming an inspiration branch and an expiration branch, a controllable outlet valve being arranged in the expiration branch.

Anesthesia systems which are convertible from partial or total rebreathing to non-rebreathing modes of operation belong to the prior art, for example in the form of realization called "Narkosespiromat" described in Bulletin 51/61 of Dragerwerk AG., 3rd edition July 1970. The conversion requires several manipulations.

A switchable anesthesia system is described in GB-PS No. 1,193,522 also in German OS No. 29 45 485. In each instance switching valves are provided which, depending on the mode of operation, close the respiratory gas cycle or open it to the outside for non-rebreathing operation.

It appears to be a disadvantage of the known switchable models that the switching to the two modes of operation is not conspicuous enough and that in several operating interventions errors may be possible which are not immediately recognized.

SUMMARY OF THE INVENTION

The invention provides an anesthetic respiratory system of an especially simple and conspicuous switching possibility between partial or total rebreathing to non-rebreathing modes of operation and thereby to increase the safety of the system. In accordance with the invention the absorber is arranged in the expiration branch and is designed as a detachable switching element, and that one point of connection of the absorber comprises a shut-off element positively actuated by the switching element, which shut-off element interrupts the ring line when the absorber is taken out and establishes separate respiration branches, and that the second point of connection of the absorber, which is open upon removal, lies behind the controllable outlet valve.

In this design, the equipment element characteristic of the partial or total rebreathing mode of operation, namely the $CO_2$ absorber, is used directly and conspicuously as a switching element. With the $CO_2$ absorber connected, the partial or total rebreathing mode of operation exists in any case, while with the $CO_2$ absorber removed, it can be assumed with certainty that the system now operates in non-rebreathing mode of operation. Such an arrangement is easy to construct and excludes the danger of operating errors.

For inserting and detaching the absorber it it appropriate to provide quick-action elements at the points of connection. Such quick-action elements are designed advantageously for example, as snap-in plug connections. This makes it possible to connect and disconnect the absorber with a single manipulation and at the same time to carry out the switching to the desired mode of operation.

By applying a clearly perceptible component, which, is desired, may be accommodated in an easy-to-see accessory housing attachable to the basic housing of the anesthetic respiratory system, the operator is conspicuously informed about the selected mode of operation. Switching is possible also during performance of the anesthesia, whereby the flexibility of the system is increased.

Another advantage can, if desired, be achieved in that the absorber is designed as a canister divided into two chambers by a partition with passage gap, and that at both points of connection identical connection elements are provided in such a way that attachment of the absorber with the points of connection interchanged is possible. With such a symmetrical construction the lime filling in the two chambers can be utilized better. When the lime in the first chamber is used up, the absorber, which is easy to detach from the points of connection at the housing, can be rotated 180° and reconnected, whereby a preferential utilization of the lime in the sub-chamber on the inlet side occurs.

In accordance with the invention, an anesthetic respiratory system is provided which is switchable between a half-open and a half-closed mode of operation. It comprises a closed ring line which contains a $CO_2$ absorber and forms an inspiration gas branch and an expiration gas branch. A controllable outlet valve is arranged in the expiration branch and the $CO_2$ absorber is arranged in the expiration branch. The expiration branch has spaced connecting points and the absorber comprises a switching element which is detachable from the connecting points. One connection point of the absorber includes a shut-off element positively actuated by a switching element so that upon removal of the absorber it interrupts the ring line and establishes separate inspiration and expiration respiration branches. The second point of connection of the absorber is opened upon removal of the absorber and is located downstream of the controllable outlet valve. Accordingly it is an object of the invention to provide an improved respiratory system which includes a $CO_2$ absorber which is detachable from a ring line so that the respiratory gas flow may be either through the absorber or through a control connecting line.

A further object of the invention is to provide an anesthetic respiratory system which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments are illustrated.

DESCRIPTION OF THE PREFERRED EMBODIMENTS

Figure 1:
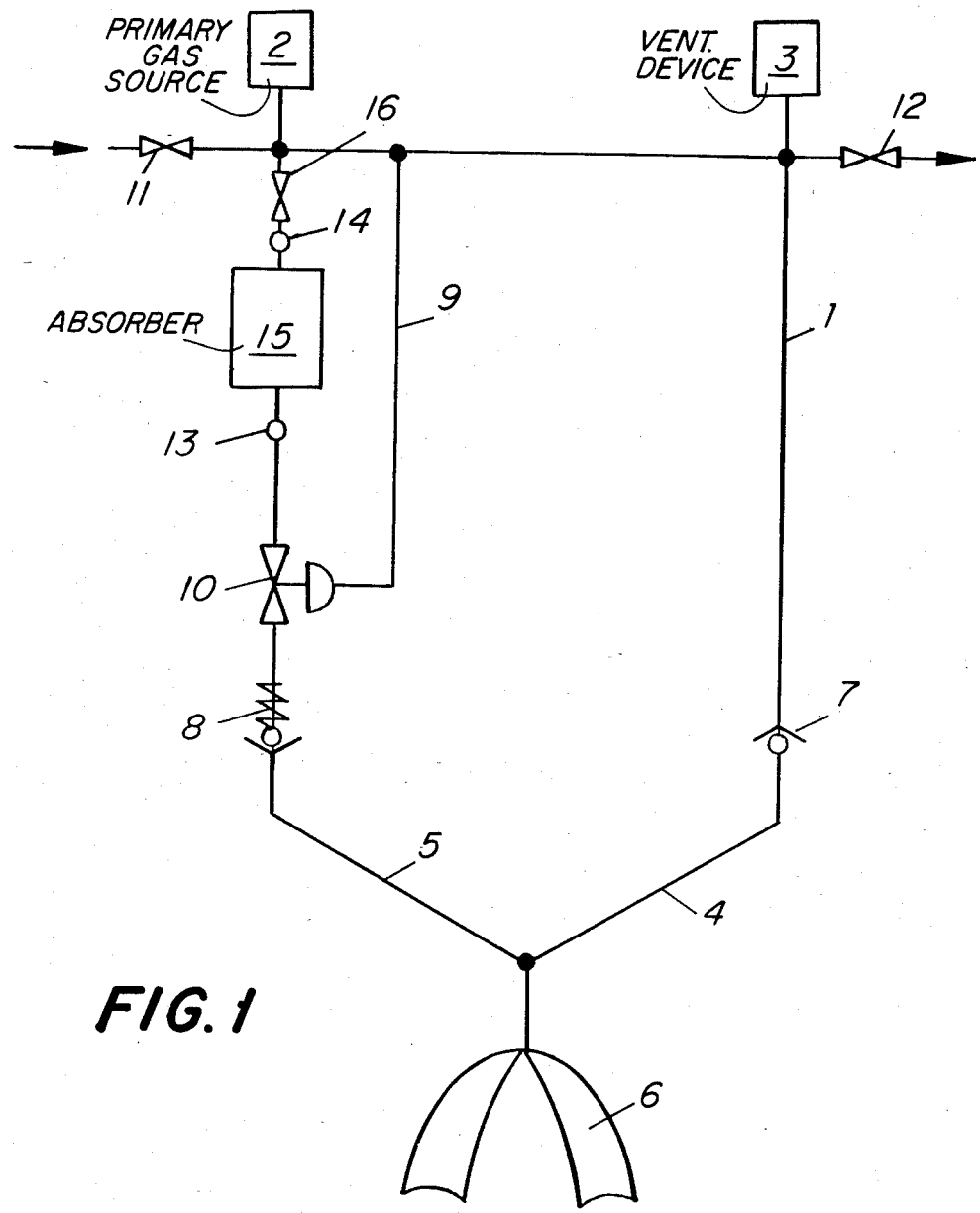
FIG. 1 is a schematic layout for the anesthetic respiratory system according to the invention.

In FIG. 1 a ring line 1 is shown, into which primary gas is fed from a primary gas source 2 or through a ventilation device 3 (or manual ventilation bag). In the two respiratory gas branches 4 and 5, check valves 7 and 9 are located before the patient exit 6. In addition, an outlet valve 9 controllable via a connecting line 9 by the ventilation pressure is arranged in the expiration branch 5.

For safety reasons a secondary air valve 11 and an adjustable overpressure valve 12 are provided. The secondary air valve 11 permits the feeding of atmospheric air into the ventilation system if the primary gas supply is not sufficient, and the overpressure valve 12 permits pressure compensation or equalization at undue pressure increase on the supply side. In flow direction after the outlet valve 10 there is an absorber 15 designed as a detachable switching element connected at two connection points 13,14.

In non-rebreathing mode of operation, the inspiration branch 4 is supplied with primary gas from the primary gas source 2 or through the ventilation device 3. During inspiration by squeezing the bellows of the ventilation device or of the manual ventilation bag, respiratory gas is conveyed to the patient 6 via the check valve 7. This causes a pressure to build up in the control line 9 which closes the outlet valve 10. The patient is ventilated with respiratory gas. During expiration by expansion of the bellows or of the manual ventilation bag, the pressure in the control line 9 drops, and the check valve 8 as well as the outlet valve 10 are now opened. Thus the expiration gas escapes from the patient 6 via the connection point 13 which is open or connected with a narcotic gas discharge line.

In this mode of operation the absorber 15 is taken out, and thereby the connection point 14 is closed by a positively actuated shut-off element 16, so that there exist two separate respiration branches 4,5 instead of a closed ring line 1.

For changeover to the partial or total rebreathing mode of operation, the crucial element, namely the absorber 15, is inserted between the connection points 13,14. The shut-off element 16 then necessarily opens at connection point 14 and combines the two respiration branches 4,5 to a closed ring line 1, into which primary gas can be fed from the primary gas source 2.

Figure 2:
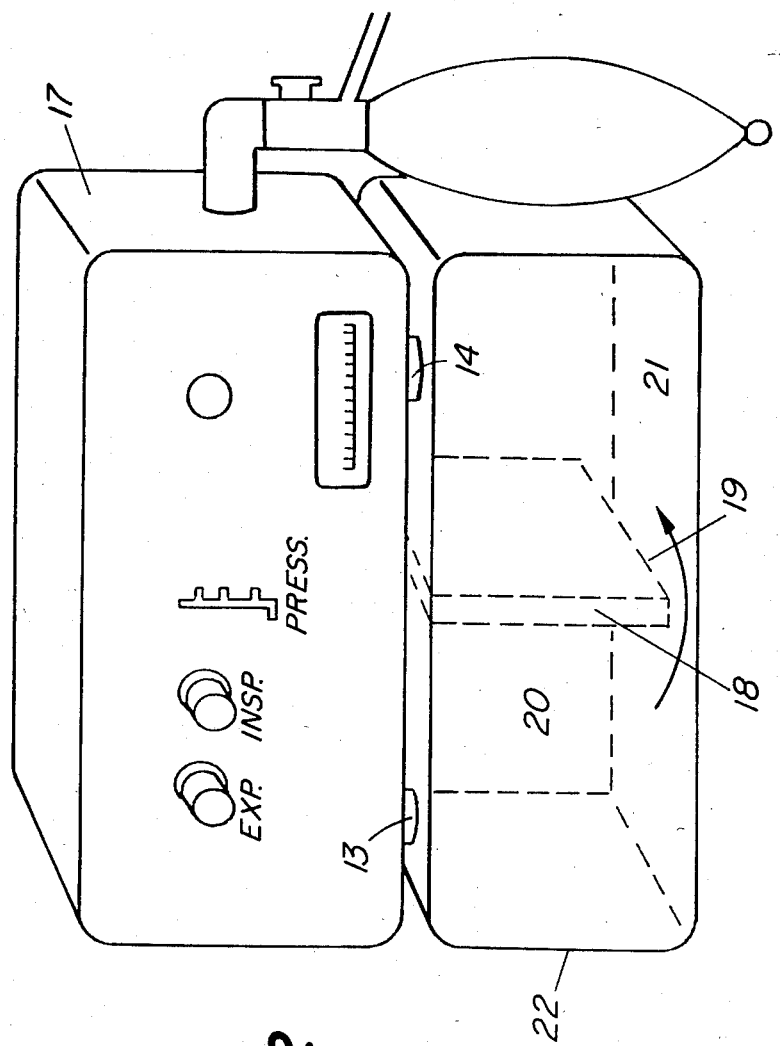
FIG. 2 is a perspective front view of an anesthesia equipment for use of the anesthetic respiratory system.

In FIG. 2, a model is represented in which the anesthetic respiratory system is lodged in a basic housing 17. The absorber 15 is here designed as a canister 22 having the same width and depth dimensions as the basic housing 17 of the anesthetic respiratory system. Thereby an especially conspicuous easy to see indication of the existing mode of operation is obtained.

At the connection points 13,14 are located snap-in elements which permit gastight connection. At point 14 a check valve is provided as a positively actuated shut-off element 16. Point 13 contains a quick-action element which can be connected with an adapted connecting element of a narcotic gas discharge line.

As the internal construction of canister 22 shown in broken lines indicates, two chambers 20 and 21 separated by a partition 18 are provided which communicate through a passage gap 19 at the bottom of the canister. Both chambers 20 and 21 contain a filling of absorber material which also fills the passage gap 19. By turning the canister 22 180° it is possible to connect chamber 21, located at first on the outlet side, now on the inlet side, so that a better utilization of the absorber filling is obtained.

While specific embodiments of the invention have been shown and described in detail to illustrate the application of the principles of the invention, it will be understood that the invention may be embodied otherwise without departing from such principles.

What is claimed is:

1. An anesthesia system for inhalation narcoses which is switchable from partial or total rebreathing to non-rebreathing modes of operation, comprising a ring line connected to a patient outlet forming an inspiration gas branch and an expiration gas branch, one-way valve means in each said inspiratory and expiratory branches for directing gas flow from said inspiratory gas branch to said patient connection and from said patient connection to said expiratory gas branch, a controllable outlet valve mounted in said expiration gas branch downstream of said one-way valve means, a $CO_2$ absorber mounted in said expiration branch downstream of said outlet valve, said expiration branch having spaced apart connection points, said $CO_2$ absorber having an inlet and an outlet detachably mounted to said connection points, one connection point being downstream of said absorber including a shut-off element including means positively actuated by the removal of said absorber from said ring line which thereby interrupts said ring line and establishes separate expiration and inspiration branches of said respiration line, said second point of connection of said absorber being opened upon removal of said absorber and being located upstream of said absorber and downstream of said controllable outlet valve, gas source means connected to said ring line downstream of said one connection point for providing an increased pressure in said ring line during an inspiratory phase and a decreased pressure during an exhalation phase, pressure relief valve means connected to said ring line downstream of said one connection point and means responsive to said increased pressure for closing said controllable outlet valve.

2. An anesthesia system according to claim 1, wherein said absorber comprises a container having a face with said inlet and outlet mounted thereon, a housing having said ring line mounted therein and including a face with said first and second connections points mounted thereon, said inlet and outlet of said absorber being removably mounted to said first and second connection points, respectively.

3. An anesthesia system according to claim 2, wherein said connection points and absorber inlet and outlet comprise snap-in plug type connections.

4. An anesthesia system according to claim 2, wherein said absorber container comprises a cannister divided into two chambers, with partitions separating each of said chambers leaving a gap between said partition and the wall of said $CO_2$ absorber container, said inlet and outlet being connected into said chambers, respectively, said inlet and outlet of said absorber and said connecting points being interchangeable so as to vary the succession of flow in said chambers.

* * * * *